(12) United States Patent
Vallin et al.

(10) Patent No.: US 6,568,850 B2
(45) Date of Patent: May 27, 2003

(54) X-RAY IMAGING SYSTEM

(75) Inventors: Asa Vallin, Stockholm (SE); Samuel Pakvis, Farsta (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 10/095,817

(22) Filed: Mar. 12, 2002

(65) Prior Publication Data

US 2002/0136356 A1 Sep. 26, 2002

(30) Foreign Application Priority Data

Mar. 22, 2001 (SE) .................................. 0101001

(51) Int. Cl.⁷ .................................................. H05G 1/02
(52) U.S. Cl. .......................................... 378/205; 378/205
(58) Field of Search .................................. 378/195–205

(56) References Cited

U.S. PATENT DOCUMENTS

| | | | |
|---|---|---|---|
| 4,071,758 A | 1/1978 | Steinbichler | |
| 5,155,757 A | * 10/1992 | Sakaniwa et al. | 378/197 |
| 5,425,069 A | 6/1995 | Pellegrino et al. | |
| 5,499,284 A | 3/1996 | Pellegrino et al. | |
| 6,106,152 A | 8/2000 | Thunberg | |
| 6,334,708 B1 | * 1/2002 | Kosugi | 378/197 |

FOREIGN PATENT DOCUMENTS

EP 0 535 378 4/1993

OTHER PUBLICATIONS

MOBILETT Plus HP Instructions for use, Siemens Elema AB (2000).

* cited by examiner

*Primary Examiner*—Craig E. Church
(74) *Attorney, Agent, or Firm*—Schiff Hardin & Waite

(57) ABSTRACT

An X-ray imaging system has an X-ray head containing an x-ray source which emits an X-ray beam. The head is rotatable around a pair of orthogonal axes for orienting the emitted X-ray beam in space. A pair of head angle sensors are located with the X-ray head, each being associated with a different one of the pair of axes for measuring an angle of inclination of the X-ray head dependent on its rotation around its associated axis. A display is operably connected to each head angle sensor through a signal processing unit for providing a graphic displaying of angle information related to each of the measured angles collocated at a single viewing station.

5 Claims, 5 Drawing Sheets

X-RAY IMAGING SYSTEM

BACKGROUND OF THE INVENTION

1. Field of the Invention

The present invention relates to an X-ray imaging system of the nonintegrated type having an X-ray head or radiator containing an X-ray source for generating an X-ray beam, the head being rotatable for orienting the X-ray beam in space, and a planar X-ray imaging device having no mechanical connection with the X-ray head.

2. Description of the Prior Art

In X-ray examinations of patients it is important for the X-ray beam which is emitted from the X-ray source to strike the X-ray film or other planar imaging device, such as a digital image receiver, at the correct angle after passage through that part of a patient that is to be radiographed, so that the resultant image is un-distorted. To achieve this it is important that the imaging device and X-ray head be properly orientated relative to each other (usually so that a central ray from the X-ray source strikes the imaging device perpendicular to the plane of its imaging surface). A known mobile X-ray imaging system, such as that described in the brochure MOBILETT™ Plus HP "Instructions for Use" of the company Siemens-Elema AB, is used with a film cartridge (or cassette) which has no mechanical connection with the X-ray head. This film cartridge is placed under the patient, often under the mattress on which the patient rests, and an operator is able to rotate the X-ray head around two mutually perpendicular rotational axes until the X-ray source and the cartridge are properly orientated with respect to one another.

To facilitate this orienting it is known from the MOBILETT to provide a head angle sensor having a ball, movable in an arcuate ball-race (or groove) and overlaid with a see-through display having angles marked on its surface corresponding to angles of inclination of the head from the horizontal. The actual angle of inclination of the head is indicated by the visual correspondence of ball and an angle mark. This means that in order to achieve an accurate reading of the angle from the display the operator must be standing substantially directly in front of the display. Such an angle sensor is placed on each of two mutually perpendicular outer wall sections of the X-ray head to respectively measure the degree of rotation of the head with respect to the horizontal around each of the two mutually perpendicular rotational axes. In use, an operator measures the angle of inclination (desired angle) of the planar imaging surface to the horizontal around each of a pair of axes corresponding to the rotational axes of the X-ray head and then, with the aid of the angle sensors, inclines the head to the same degree so that the central ray of the X-ray beam is perpendicular to the planar imaging surface of the imaging device.

One problem with such an arrangement is that the angle information is displayed at two separate viewing stations, perpendicular to one another. This means that the operator cannot see angle information for both angles of inclination of the X-ray head at the same time and must move around the imaging system to verify each of the angles of inclination of the head. Furthermore the operator must remember the desired angles which only adds to the burden of the operator when setting up the system.

As used herein the term "viewing station" means a region of or on the external surface of X-ray imaging system at which one or more displays are situated with the intention to be viewable from a single operator location.

SUMMARY OF THE INVENTION

An object of the present invention is to provide an x-ray imaging system which avoids the above-discussed problem of inclination information being displayed at separate viewing stations which are not simultaneously observable.

The above object is achieved in accordance with the principles of the present invention in an x-ray system having an x-ray head containing an x-ray source which emits an x-ray beam, the head being rotatable around a number of axes for orienting the emitted x-ray beam in space, and having a number of head angle sensors located with the x-ray head, respectively for the different axes, which measure an angle of inclination of the x-ray head dependent on the rotation around the associated axis, each head angle sensor being connected to a display for displaying angle information related to the measured angles, and wherein each head angle sensor provides an output signal indicative of the measured angle, the display receiving these output signals and providing a graphic display of the angle information for each head sensor together at a single viewing station.

By providing angle sensors, such as accelerometers or inclinometers, which each have an output signal dependent on the sensed angles, then respectively associated displays which provide a graphic display of angle information dependent on the output signal can be readily allocated together at a single viewing station, independent of the location of the angle sensors.

Preferably, a difference former is provided which generates a signal indicative of a difference between the angle measured by each sensor and a corresponding desired angle of inclination, for example entered by an operator via a user interface such as a keypad or entered automatically from angle sensors at the X-ray imaging device, for supply to and use by the displays to provide a visual indication of the differences.

DESCRIPTION OF THE PREFERRED EMBODIMENTS

Figure 1:
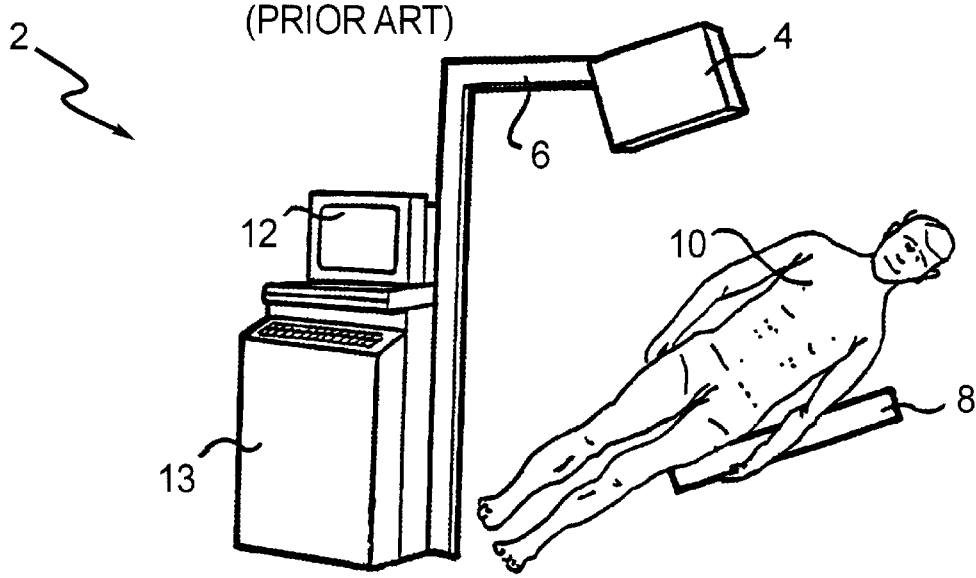
FIG. 1 illustrates a known non-integrated X-ray imaging system in use.

Referring to FIG. 1, a non-integrated X-ray imaging system 2 is shown having a rotatable X-ray head 4 carried by an arm 6 and a mechanically separate planar X-ray imaging device 8, such as a film cartridge or a digital imaging array, for recording an image of a patient 10 beneath whom it is located. The imaging device 8 is shown inclined at an angle to the horizontal. The X-ray head 4 contains an X-ray source (not shown) with which an X-ray exposure of the patient 10 can be carried out. A computer system 12 provides a user interface via which information, such as for controlling the duration and energy of an X-ray beam produced by the X-ray source, may be entered into a power supply/control unit 13 of the system 2, which is responsive to the input to vary the power it supplies to the X-ray head 4.

Figure 2:
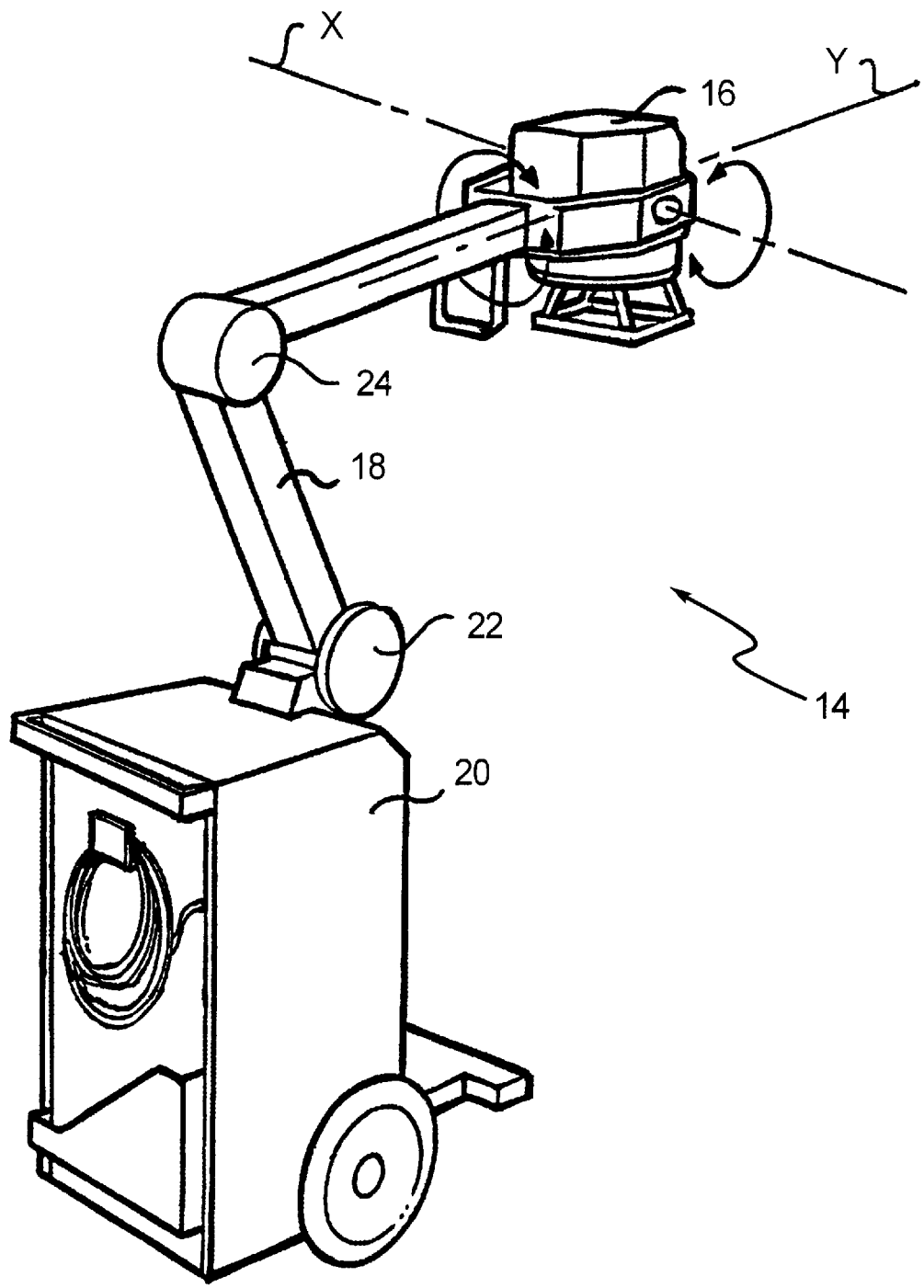
FIG. 2 illustrates a known mobile X-ray generator together with the pertinent rotational axes for the X-ray head.

A mobile X-ray generator 14 is shown in FIG. 2. This type of generator 14 is usually provided to be rolled to a bed of the patient when an X-ray image is needed. An X-ray head 16 is located at one end of an arm 18 and may be effectively adjusted vertically and horizontally with respect to a control/power supply unit 20 by rotation of the arm 18 about a first pivot axle 22 and a second pivot axle 24. Importantly for the system according to the present invention the X-ray head 16 is mounted for independent rotation about each of two orthogonal axes X and Y, as shown by the arrows.

Figure 3:
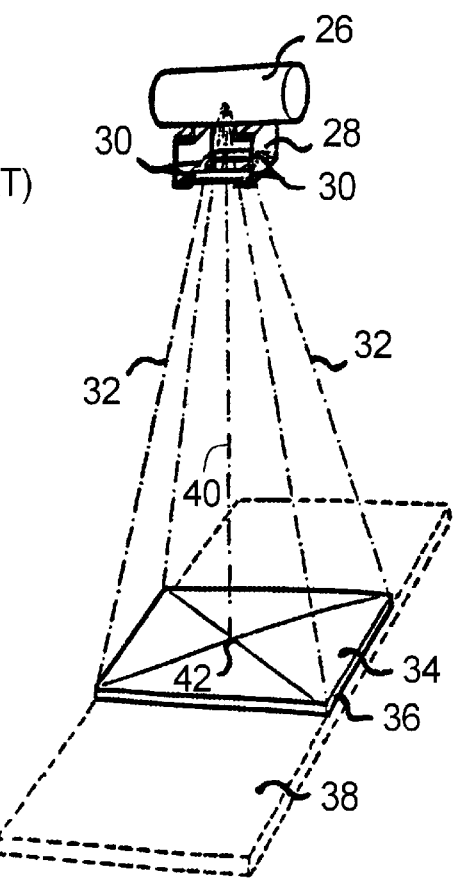
FIG. 3 is a schematic of the illumination of the X-ray imaging device by an X-ray beam from the X-ray head.

As is well known in the art and as is shown in FIG. 3, the X-ray head 16 contains an X-ray source, such as an X-ray tube 26 with a collimator 28 in the form of movable diaphragm plates 30 with which a generally rectangular X-ray beam 32 can be generated. The X-ray beam 17 is oriented in centered fashion on a planar, typically rectangular, imaging surface 34 of an imaging device, such as a film cartridge 36 that is arranged on an examination table (or patient bed) 38. The preferable and most common mutual orientation of the head 16 and imaging surface 34 is illustrated in FIG. 3. wherein the central ray 40 of the X-ray beam 32 strikes the mid-point 42 of the planar imaging surface 34 perpendicularly to that surface 34.

Figure 4:
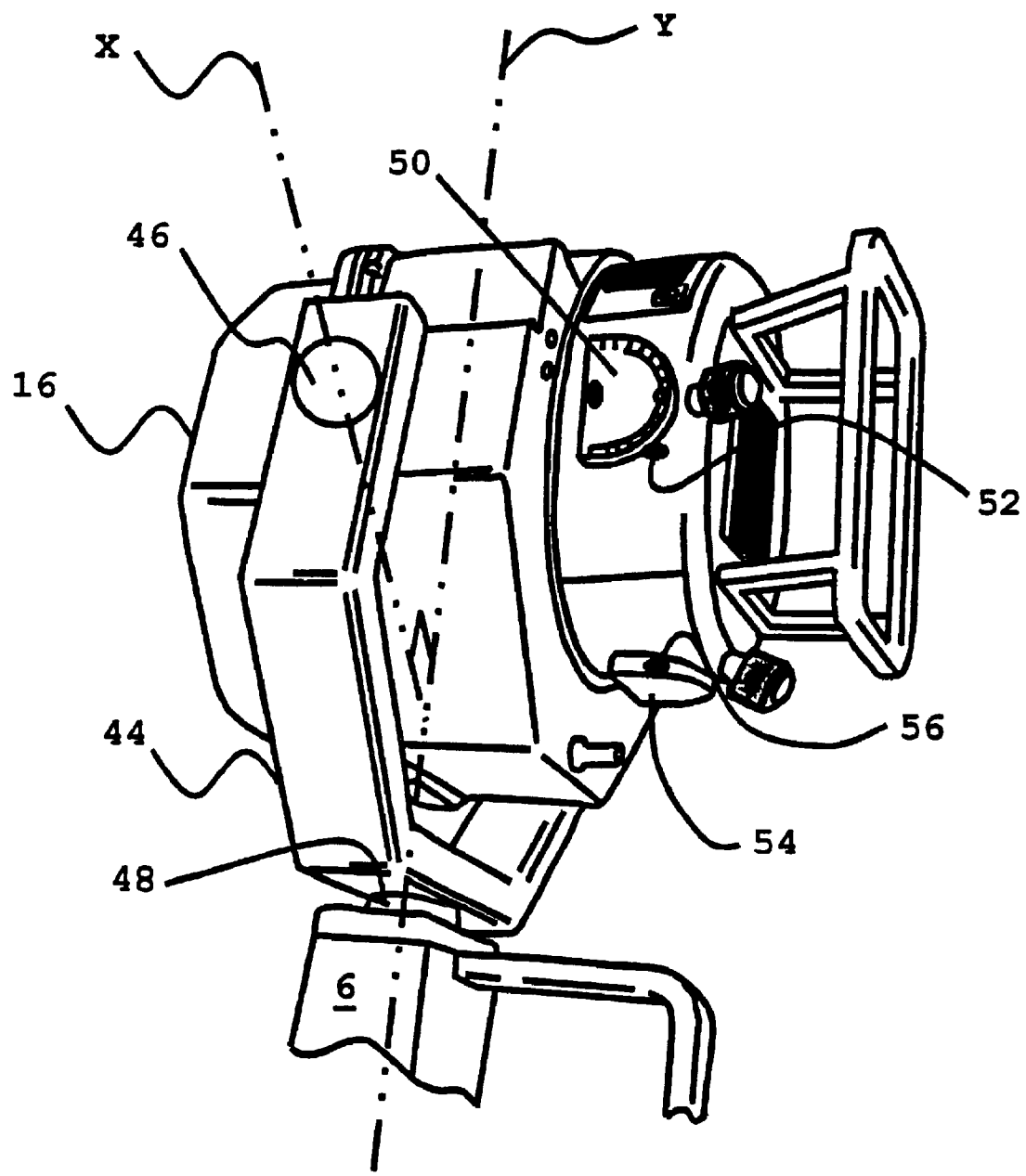
FIG. 4 illustrates a known angle sensor used with the X-ray head of FIG. 2.

To aid in the mutual orientation it is known to provide the head 16 of the system of FIG. 2 with head angle sensors, as shown in FIG. 4. The head 16 is mounted in a cradle 44 by means of a rotational mount 46 for rotation of the head 16 about the axis X. The cradle 44 is itself rotatable about an axle 48 connected to the arm 6 for rotation of the head 16 about the axis Y which is perpendicular to the other axis X. A first known head angle sensor 50, of the ball type as described with regard to the MOBILETTE system above, is mounted on an external surface of the head 16 at a first viewing station 52 for providing a display of the angle of inclination of the head 16 to the horizontal dependent on rotation about the associated axis X. A second known head angle sensor 54 is mounted on an external surface of the head 16 at a second viewing station 56 to be perpendicular to the first sensor 50 and provides a display of the angle of inclination of the head 16 to the horizontal dependent on rotation about the associated axis Y. As can be seen from the figure an operator cannot read both head angle sensors 50, 54 from a single operating location.

Figure 5:
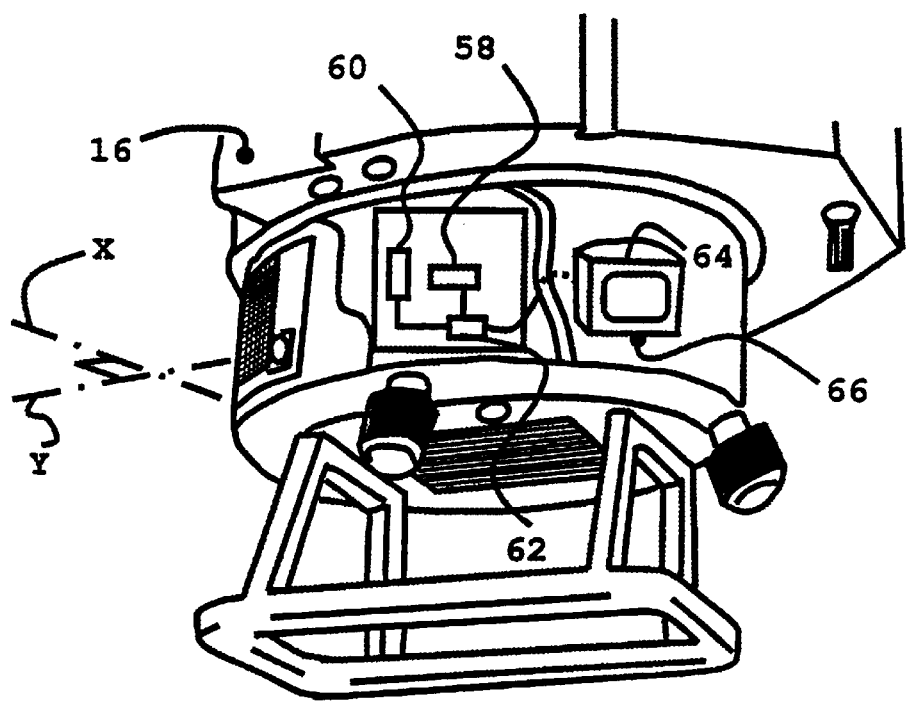
FIG. 5 illustrates a portion of the X-ray head of FIG. 2 adapted according to the present invention showing internally disposed head angle sensors.

A non-integrated X-ray imaging system according to the present invention for example, as illustrated in FIG. 2, has an X-ray head 16 substantially similar to that illustrated in that figure and FIG. 4 except that the angle sensors 50, 54 have been removed and replaced with known angle sensors having an electrical signal output indicative of a detected angle of inclination, such as first and second accelerometers or inclinometers 58, 60 illustrated schematically in FIG. 5. These head angle sensors 58, 60 are arranged to measure inclinations of the head 16 as occur with rotations around the X and Y axes respectively, to provide functional equivalence with known angle sensors 50, 54. FIG. 5 shows a portion of the X-ray head 16 showing the first and the second head angle sensors 58, 60 located internally of the head 16 with their outputs connected to a processing unit 62 which may include the functionality of a difference forming means as described below and which drives a display 64. The display 64 is here illustrated as a visual display unit such as an LCD unit but may be of the type described below with reference to FIG. 6, and is driven by the processing unit 62 to display angle information dependent on the angles measured by the first and second head angle sensors 58, 60. The display 64 thus acts to present angle information from each of the head angle sensors 58, 60 at a single viewing station 66, which is here shown to be an external wall section of the head 16. Alternatively, one or both of the processing unit 62 and the display 64 can be located in or on the power/control unit 20 of the imaging system of FIG. 2. It will be appreciated that the display 64 may also be formed by two displays in a side-by-side arrangement (not shown), one associated with each angle sensor 58, 60, while still being at a single viewing station 66.

Figure 6:
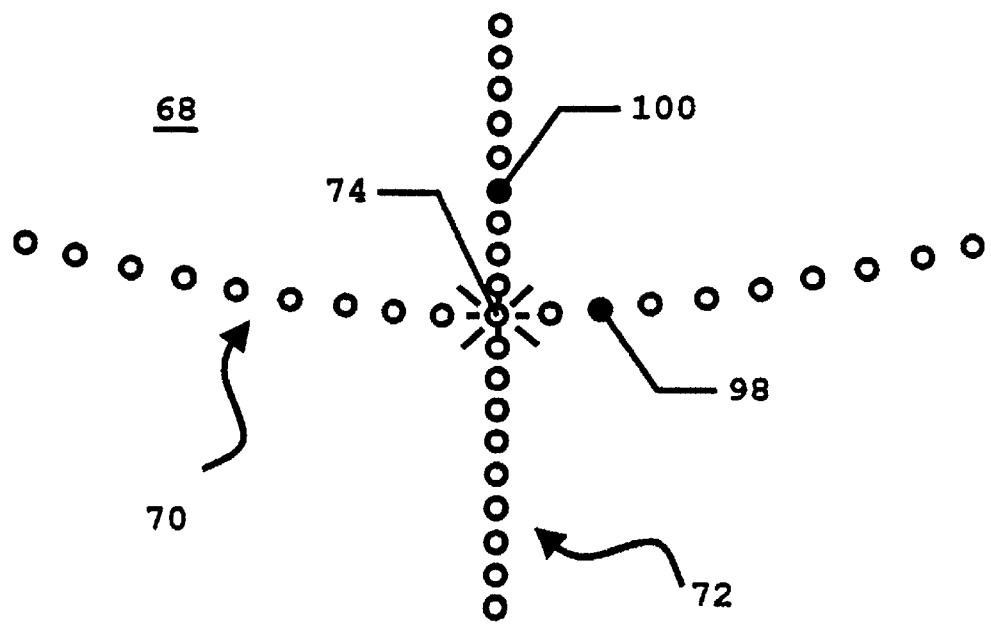
FIG. 6 illustrates a display for showing angle information dependent on the outputs of the sensors of FIG. 5

A further form of the display 68 is shown in FIG. 6, which is particularly useful for displaying differences between an actual angle of inclination, as measured by a one of the head angle sensors 58, 60, and a corresponding desired angle of inclination, as described in more detail below, to intuitively guide an operator to vary the inclination of the X-ray head 16 to achieve the proper orientation. The display 68 has a first linear array 70 of individually actuable light emitting diodes (LEDs) intersecting with and substantially perpendicular to a second linear array 72 of LEDs. The LED 74 common to each array 70, 72 is here arranged to be the middle LED of each of the arrays 70, 72. When the arrays 70, 72 are employed to display the differences, this middle LED illuminates to indicate correct alignment (zero angular difference between the head 16 and imaging device). The operation of this display 68 is explained in greater detail below with regard to the non-integrated X-ray imaging system shown in FIG. 7.

Figure 7:
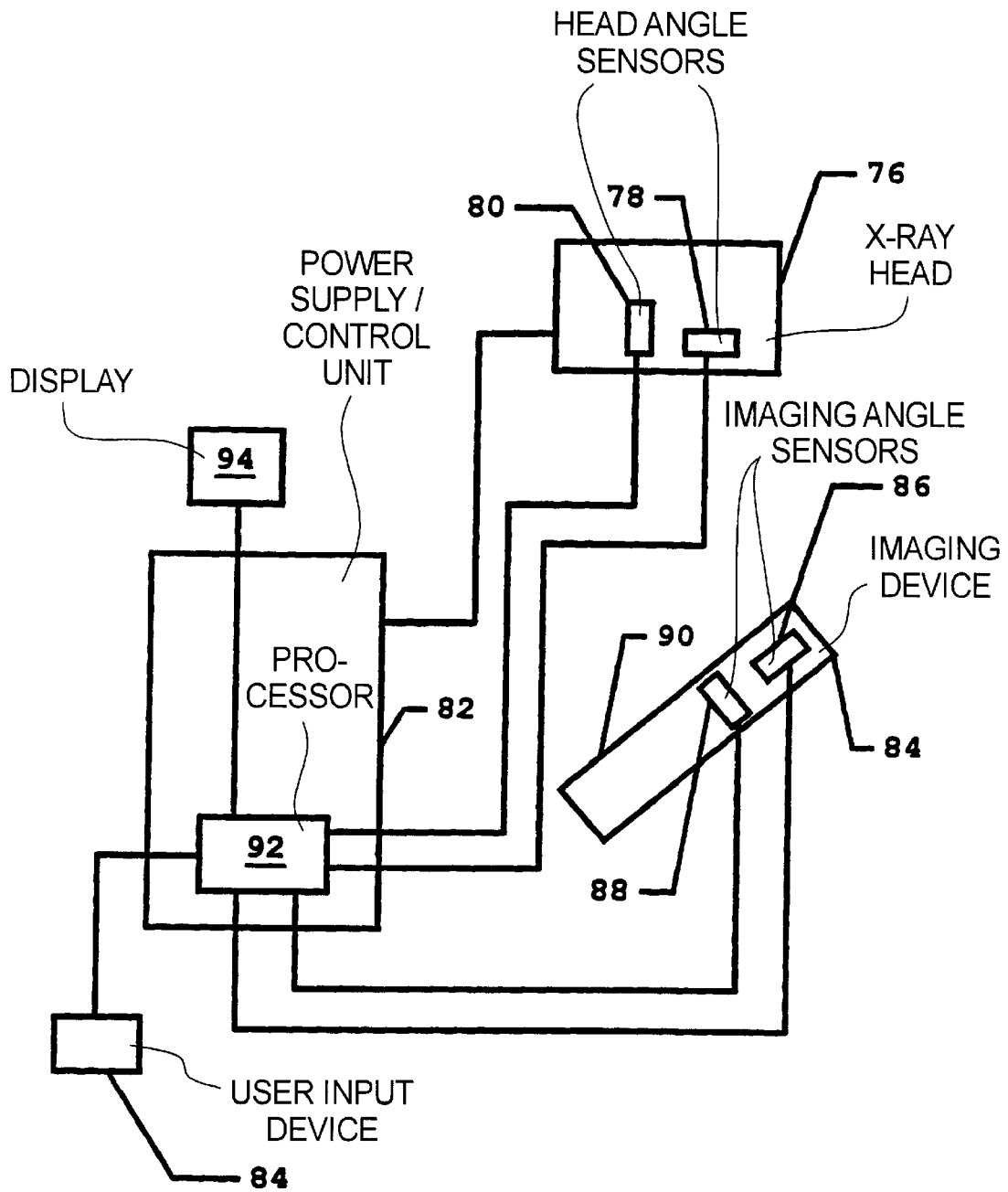
FIG. 7 is a block diagram of an embodiment of a non-integrated X-ray imaging system according to the present invention.

Considering FIG. 7, an X-ray head 76, such as that shown in FIG. 2, contains first and second head angle sensors 78, 80 for measuring respective angles of inclination of the head 76 to the horizontal for rotation of the head 76 about respective perpendicular axes X and Y, as described above. The head 16 is operably connected to a power/control unit 82 which provides power to energize an X-ray source (not shown) within the head 16. An imaging device 84, such as a digital imaging array or a film cartridge, is also provided in non-mechanical connection with the imaging head 76 so as to be mutually independently orientable. A first imaging angle sensor 86 and a second imaging angle sensor 88 are located with the imaging device 84, each providing an output signal indicative of the inclination of a planar imaging surface 90 of the imaging device 84 to the horizontal to complement those angles measured by the head angle sensors 78, 80. The angles measured by the imaging angle sensors 86, 88 provide desired angles which are to be attained by the X-ray head 76 (as measured by the complementary head angle sensors 58, 60). Alternatively the imaging angle sensors 86, 88 may be mounted on a support which is removably locatable on the imaging device 84, preferably on or proximal with the planar imaging surface 90. Such a support may have two orthogonally arranged support bars, one for each imaging sensor 86, 88, which may be located on the imaging device 84 so as to lie substantially parallel with adjacent sides of the planar imaging surface.

A processing unit 92, such as a programmable microprocessor, is located within the power/control unit 82 and is arranged to receive signals from all sensors 78, 80, 86, 88 representative of the angles measured by each of the sensors 78, 80, 86, 88 and to form a difference between the desired angles measured by the imaging angle sensors 86, 88 and respective angles measured by the complementary head angle sensors 78, 80. A signal indicative of this difference for rotation of the head around each of the X and Y rotational axes provides a drive signal to a display 94 which is located either on the head 76 or the power/control unit 82 at a single viewing station. The display 94 responds to the drive signal by providing a visual display related to the thus formed differences. As also shown in FIG. 7 a user input device 84, such as a keypad or keyboard (with or without an associated display) is also provided, via which an operator may provide the desired angles, measured manually in a known manner, as an alternative to having the display 94 provided with imaging angle sensors 86, 88.

In the embodiment of FIG. 7 the display 94 has the two linear arrays 70, 72 of LEDs of the type described in connection with FIG. 6. The array 72 is here associated with "Y-differences", for rotation of the head 76 around the Y axis. This is the output from the second imaging angle sensor 88 minus that from the second head angle sensor 80. The array 70 is here associated with "X-differences", for rotation of the head 76 around the X axis. This is the output from the first imaging angle sensor 86 minus that from the first head angle sensor 78.

The processing unit 92 is programmed to form an X-difference and selectively activates one LED 98 in the LED array 70, the location of which one LED 98 is dependent on this X-difference. In this example the processor 92 operates to cause an individual LED 98 in the LED array 70 to illuminate, selected according to the rules:

(a) For absolute values of X-differences greater than 10 degrees each LED of the array 70 represents a variation of 10 degrees from the desired angle (represented by the central LED 74).

(b) For absolute values of X-difference less than 10 degrees each LED of the array 70 represents a variation of 1 degrees from the desired angle.

Thus as, shown in FIG. 6 the processor 92 has formed an X-difference with an absolute value of either 2 degrees or of between 20 to 29 degrees. The processing unit 92 also is programmed to form a Y-difference and selectively illuminates one LED, 100, in the LED array 72, the location of which one LED 100 is dependent on this Y-difference. In this example the processor 92 operates to illuminate an individual LED in the LED array 72 according to the rules, suitably amended for reference to the Y-difference, set out above for illuminating an individual LED in the array 70, dependent on the X-difference.

Thus as, shown in FIG. 6 the processor 92 has formed a Y-difference with an absolute value of either 4 degrees or of between 40 to 49 degrees.

The processing unit 92 is further programmed to utilize the signs of the X- and Y-differences respectively determine on which side of the central LED 74 the individual LED will be illuminated.

It will be appreciated by those skilled in the art that the resolution of the display can be readily adjusted to suit the particular application and the resolution of the angle sensors 78, 80, 86, 88 used. It will be further appreciated that the individual LED arrays 70, 72 may be readily replaced by a visual display unit driven to display individual segements each corresponding to an individual LED of the arrays 70, 72, which segments may be higlighted in a manner corresponding to the activation of an individual LED 98, 100 in each of the respective arrays 70, 72.

The common LED 74 can be operated by the processor 92 to blink until both desired angles have been attained by the X-ray head 76, at which time the illumination will become constant. This blinking provides a enhanced visual warning to the operator that the orientation of the head 76 is incorrect.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray imaging system comprising:

an x-ray head containing an x-ray source which emits an x-ray beam, said x-ray head being rotatable around a plurality of axes for orienting the emitted x-ray beam in space;

a plurality of head angle sensors, respectively associated with said plurality of axes, located with said x-ray head, each head angle sensor measuring an angle of inclination of the x-ray head relative to the axis associated therewith, and each head angle sensor generating an output signal indicative of the angle of inclination measured thereby two of said head angle sensors respectively measure angles of inclination of said x-ray head relative to two mutually perpendicular axes among said plurality of axes;

a difference former which receives the respective output signals from said head angle sensors and which calculates a difference between each angle of inclination and a corresponding desired angle of inclination, and which generates a signal dependent on the calculated difference for each axis in said plurality of axes;

a display provided with the respective output signals from said plurality of head angle sensors and generating a graphic display of the respective angles of inclination measured by each of said plurality of sensors, at a single viewing station said display comprises two linear arrays of individually actuatable display segments, said two linear arrays being respectively associated with said two mutually perpendicular axes; and said display and said difference former cooperatively activate respective segments in said two linear arrays dependent on a magnitude of the calculated difference for the respective axes.

2. An x-ray imaging system as claimed in claim 1 wherein said display is provided with said signal from said difference former and includes a visual indication of each difference in said graphic display at said single viewing station.

3. An x-ray imaging system as claimed in claim 1 further comprising an input unit for entering, for said plurality of axes, respective desired angles of inclination.

4. An x-ray system as claimed in claim 2 further comprising a planar imaging device which is mechanically separate from said x-ray head, and wherein said input unit comprises a plurality of imaging angle sensors corresponding to said plurality of head angle sensors, said plurality of imaging angle sensors being located with said imaging device and each being responsive to, and generating an output signal indicative of, an angle of inclination of the imaging device with respect to said plurality of axes for supply to said difference former as said desired angles of inclination.

5. An x-ray imaging system as claimed in claim 1 wherein said two linear arrays intersect at a single common segment, and wherein said display and said difference former cooperatively activate at least one segment in each array having a maximum displacement from said common segment dependent on said magnitude of the calculated difference for the respective axes.

* * * * *